United States Patent [19]

Morishige

[11] Patent Number: 4,839,172

[45] Date of Patent: Jun. 13, 1989

[54] COMPOSITION OF ACCELERATING RECOVERY OF FUNCTION OF HEMATOPOIETIC ORGANS

[75] Inventor: Fukumi Morishige, Fukuoka, Japan

[73] Assignee: Nissan Chemical Industries, Ltd., Tokyo, Japan

[21] Appl. No.: 737,048

[22] Filed: May 23, 1985

[30] Foreign Application Priority Data

May 26, 1984 [JP] Japan .................................. 59-106971

[51] Int. Cl.$^4$ .............................................. A61K 35/48
[52] U.S. Cl. ..................................................... 424/105
[58] Field of Search ......................................... 424/105

[56] References Cited

U.S. PATENT DOCUMENTS 3,279,991 10/1966 Kato et al. ............................ 424/105
4,396,601 8/1983 Salser et al. ............................ 424/94

OTHER PUBLICATIONS

Yuki, JA-075400, abstract, 1980. Sepg. DNA from Fishes Soft Roe-by Homogenising, Adjusting pH with Acid, Stirring, Adding Alkali, Sepg. Off Solids and Adding Acid.

Iwait, JA-088340, abstract, 1980. Extn. of Deoxyribonucleic Acid-by Treating Soft Roe of Fish with Mixed Soln. of High Concn. Inorganic Salts and Alkali.

Kimoto et al., KAKUSAN NO ELYOGAKU (Science of Nutrition of Nucleic Acid) published Aug. 25, 1983, p. 38 (English translation).

Chemical Abstracts, vol. 30, nr.21, Nov. 10, 1936, Column 7641-3; Columbus, Ohio, U.S.A.

Chemical Abstracts, vol. 66, nr.2, Jan. 9, 1967, p. 833, ref.nr. 8675s; Columbus, Ohio, U.S.A.

*Primary Examiner*—Margaret Moskowitz
*Assistant Examiner*—F. T. Moezie
*Attorney, Agent, or Firm*—Oliff & Berridge

[57] ABSTRACT

A composition for accelerating the recovery of hematopoietic function and a method of recovering the physical strength of patients by orally administering the composition are disclosed. The composition comprises a milt extract and vitamin C and/or its salt. The composition does not cause an increase of blood uric acid levels.

15 Claims, 5 Drawing Sheets

Fig. 1

(A) ——— : Nucleic Acid alone (case 1)

(B) ---- : Powder preparation as obtained in Formulation Example 1 (case 2)

(C) —·— : Powder preparation as obtained in Formulation Example 2 (case 3)

(D) --- : Powder preparation as obtained in Formulation Example 2 (case 4)

Fig. 2

(A): Powder preparation as obtained in Formulation Example 1 (case 7)

(B): milt extract (case 5)

(C): Vitamine C (case 6)

(D): control (case 8)

Fig. 3

(A): Powder preparation as obtained in Formulation Example 1 (case 7)

(B): milt extract (case 5)

(C): Vitamine C (case 6)

(D): control (case 8)

Fig. 4

(A) : Powder preparation as obtained in Formulation Example 1 (case 11)

(B) : Vitamine C (case 10)

(C) : milt extract (case 9)

COMPOSITION OF ACCELERATING RECOVERY OF FUNCTION OF HEMATOPOIETIC ORGANS

FIELD OF THE INVENTION

The present invention relates to a composition for increasing the physical strength of healthy persons or for accelerating the recovery of physical strength by patients during or after medical treatment. More particularly, it relates to a composition comprising a mixture of a milt extract and vitamin C.

BACKGROUND OF THE INVENTION

For the purpose of accelerating the recovery of physical strength by patients during or after medical treatment, particularly by patients during or after treatment for the inhibition of nucleic acid metabolism of cancer cells, such as administration of anticancer agents and radiation, one important factor is the recovery of the hematopoietic function of bone marrow.

The hematopoietic function of cancer patients, during pharmacotherapy with anticancer agents or the like or radiotherapy, is reduced. In particular, the number of blood platelets and leucocytes in the blood of such patients is significantly reduced. This reduction in hematopoietic function necessarily leads to reduced biophylaxis. For this reason, recovery of the hematopoietic function of bone marrow is contemplated to aid in the recovery of physical strength by such patients.

Accordingly, nutritional auxotherapy in addition to surgical or chemotherapeutic treatment has been proposed for the treatment of cancer. For example, it has been considered useful to administer to patients beer yeast having a high nucleic acid content as described, for example, in Kimoto et al., *Kakusan no Eiyogaku*, 52, Nihon Bunshi Seigo Eiyogaku Kenkyu Zaidan (Aug. 25, 1983).

The object of the above-described therapy is to accelerate the recovery of tissue cells by patients during or after medical treatment by means of supplementing the nucleic acid synthesis ability of tissue cells through salvage synthesis (cf. page 34 of Kimoto et al.). The therapy further aims at selective utilization of the administered nucleic acids and/or the degradation products thereof, i.e., nucleotides, nucleosides and nucleic acid bases, by normal bone marrow cells, which have been partly damaged by the administration of anticancer agents and the like rather than by cancer cells by virtue of the salvage synthesis (cf. page 38 of Kimoto et. al.).

As set forth above, the administration of drugs having a high nucleic acid content in combination with pharmacotherapy or radiotherapy is considered effective in the treatment of patients with cancer.

However, when such drugs having a high nucleic acid content are given to patients suffering from hyperoxia, there is a high possibility that uric acid levels in the blood will increase, causing complications, such as gouty arthritis, tophus, renal disorders, urolithiasis, arteriosclerosis, etc.

There has been a great need, therefore, to develop a drug having a high nucleic acid content for recovering the hematopoietic function of bone marrow thereby to restore the physical strength of patients without an accompanying rise of uric acid levels in the blood that possibly causes the above-described complications.

There also has been a need to develop a nutritive source which enables patients during medical treatment as well as healthy individuals to easily recover physical strength by accelerating recovery of the function of the hematopoietic organs.

SUMMARY OF THE INVENTION

Accordingly, an object of the present invention is to provide a medical composition for accelerating recovery of the physical strength of healthy persons or patients during or after medical treatment and a method of using the same.

Another object of the present invention is to provide a medical composition which can prevent reduction of platelets and leucocytes in blood caused by the administration of anticancer agents or radiotherapy for the inhibition of nucleic acid metabolism of cancer cells, thereby to accelerate recovery of the hematopoietic function of bone marrow, and a method of using said composition.

It was discovered that fish milt extract has a high content of nucleic acids and that nucleic acids are present in fish milt extract in combination with proteins together with a sugar portion and a mineral. It also was found that functional recovery of hematopoietic organs can satisfactorily be achieved and that the uric acid level in blood can be decreased by orally administering a combination of such a milt extract with vitamin C and/or a pharmaceutically acceptable salt thereof.

DETAILED DESCRIPTION OF THE INVENTION

The milt extract which is useful in the present invention comprises from 25 to 50 weight % of a deoxyribonucleic acid, from 25 to 50 weight % of a protein such as a histone or a protamine and has a nitrogen content of from about 13 to 20%.

The composition according to the present invention comprises a mixture of the above-described milt extract, vitamin C and/or a pharmaceutically acceptable salt thereof.

The milt extract has a high content of nucleic acids, which are present in the form of a nucleic acid-protein combinations. The milt extract additionally contains sugars and inorganic matters. These inorganic matters, or minerals, are the residual inorganic ash components of the milt extract. When the milt extract is mixed with vitamin C or its salt, these components together exhibit a remarkable effect of accelerating recovery of the hematopoietic function of hematopoietic organs, particularly bone marrow.

Despite the high nucleic acid content of the milt extract, the composition according to the present invention, when orally administered, suppresses an increase of uric acid levels in the blood serum of patients suffering from hyperoxia and, at the same time, prevents reduction of blood platelet and leucocytes as apparently demonstrated in the clinical examples hereinafter described. Therefore, the composition of the present invention is effective to aid in recovery of the physical strength of patients without causing complications, such as gouty arthritis, tophus, renal disorders, urolithiasis, arteriosclerosis, etc.

When the composition of the present invention is orally administered, a portion of the nucleic acids contained in the milt extract are degraded to nucleotides, nucleosides and ultimately nucleic acid bases by the time of intestinal absorption as described on pages 27–28 of Kimoto et al. More specifically, orally administered nucleic acids are hydrolyzed by ribonuclease and deoxyribonuclease in pancreatic juices to form nucleotides. Nucleotides are then degraded to nucleosides through release of phosphoric acid by the action of phosphatase. Nucleosides are further decomposed into nucleic acid bases and pentoses by nucleosidase. The nucleic acids are assumed to be absorbed from an intestine in the form of any of these degradation products.

Therefore, in the salvage synthesis of nucleic acids, it is anticipated that the effect of the orally administered nucleic acids can also be exerted by orally administering nucleotides, nucleosides and nucleic acid bases.

The milt extract which is useful in the composition according to the present invention can be obtained by extracting milt from fish, particularly from salmons, porgies, herrings, cods, sardines, swellfishes, bonitoes, etc., as follows. A milt, for example of salmon, is filtered to remove any solid matter, such as the membrane, and to the filtrate is added a 0.14 mol/l aqueous solution of sodium chloride, followed by grinding and stirring to obtain a milky suspension. The suspension is centrifuged to separate the supernatant liquor. The solid phase thus obtained is then washed with a 0.14 mol/l aqueous solution of sodium chloride, followed by filtration. The above-described procedures from suspension through filtration are repeated two or three times. The finally obtained filtrate is washed with ethanol to remove ethanol-soluble organic matters and water, and is then dried under reduced pressure to obtain the desired milt extract.

The milt extract thus obtained from salmon has the following chemical and physical properties:

| Weight Ratio of Nucleic Acid to Protein: | from 1.0:1.0 to 2.0:1.0 |
| --- | --- |
| Nucleic acid content: | 25–50 wt % |
| Protein Content: | 25–50 wt % |
| Mineral Content: | 5–15 wt % |
| Total Nitrogen Content: | 13–20 wt % |
| Ninhydrin Reaction: | positive |

Milt extract prepared from other fish, e.g., from porgies, herrings, cods, sardines, swellfishes, bonitoes, saurels, trout, etc., have substantially the same chemical and physical properties as shown above.

Thus, the milt extract which is useful in the present invention can be regarded as a nucleic acid-rich, nucleic acid-protein combination.

Vitamin C or its pharmaceutically acceptable salt, including synthetic vitamin C and naturally-occurring vitamin C and their alkali metal salts, e.g., a sodium salt, a potassium salt, a calcium salt, etc., can be used as another component in the composition of the present invention. The vitamin C and its salt may have a high purity up to 100%. They may also be derived from juices of vegetables or fruits, e.g., a mandarin orange, a lemon, a grapefruit, etc., or concentrates thereof.

The composition of the present invention comprises a mixture of the above-described milt extract and vitamin C and/or its salt, wherein the weight ratio of vitamin C and/or a salt thereof to the milt extract can be selected so that vitamin C and/or its salt may be present in an amount sufficient to prevent reduction of platelets and leucocytes in blood and to inhibit an increase of uric acid levels in blood. More specifically, the weight ratio of vitamin C and/or its salt to the milt extract ranges from 1:1 to 100:1.

The composition according to the present invention is orally administered in any of solid, fluid or liquid dose forms. The solid preparations may comprise solely the mxiture of the milt extract and purified or crude (inpurified) vitamin C. The solid dose form may also be prepared by adding at least one pharmacologically acceptable binder (e.g., syrups, gum arabic, gelatin, sorbitol, tragacanth, polyvinylpyrrolidone, etc.), vehicles (e.g., lactose, sugar, corn starch, calcium phosphate, sorbitol, glycine, etc.), lubricants (e.g., magnesium stearate, talc, polyethylene glycol, silica, etc.), disintegrators (e.g., potato starch, etc.), or seasonings (e.g., sweeteners, salt, flavors, amino acids, e.g., sodium glutaminate, etc.) to the mixture according to the present invention and formulating the mixture in a known manner into powders, granules, tablets, capsules, etc.

The fluid or liquid preparations may comprise solely the mixture according to the present invention, or may be prepared by adding water and, if desired, seasonings (e.g., sweeteners, edible salt, flavors, amino acids, e.g., sodium glutaminate, etc.) to the mixture.

The dose level of the milt extract in the novel mixture of the present invention is in the range of from 0.1 to 10 g, and preferably from 0.2 to 5 g, per day for an adult, and the dosage of the mixture is in the range of from 1 to 50 g, and preferably from 10 to 40 g, per day for an adult in a single or 3 divided doses. The above-specified dosage may be varied depending on the age, body weight, symptoms and the like of the individual.

Since the composition of the present invention markedly prevents reduction of blood platelets and leucocytes, which is particularly observed in patients suffering from cancers who receive continuous administration of anticancer agents, and also inhibits the increase of uric acid levels in blood, it accelerates the recovery of the hematopoietic function of bone marrow without being accompanied by complications, such as gouty arthritis, tophus, renal disorders, urolithiasis, arteriosclerosis, etc. The composition of the present invention thus makes a great contribution to recovery of the physical strength of such patients.

Hence, the method comprising orally administering the composition of the present invention to patients, particularly during or after medical treatment for cancer, offers an excellent nutritional auxotherapy.

Further, the above-described method of using the composition of the present invention is also applicable to recovery of the physical strength of healthy persons as well.

The present invention will now be illustrated in greater detail by referring to the following examples.

PREPARATION EXAMPLE 1

211 grams of milt obtained from salmon were ground and filtered to remove solid matter including the membrane. To the filtrate was added 1.5 liters of a 0.14 mol/l aqueous solution of sodium chloride and the mixture was ground and stirred to form a milky suspension. The suspension was subjected to centrifugation, and the supernatant liquor was separated. To the solid phase thus obtained was added 1.5 liters of a 0.14 mol/l aqueous solution of sodium chloride for washing, followed by filtration. These procedures involving suspension, centrifugation, washing and filtration were repeated 2 to 3 times. The resulting filtrate was washed with ethanol to remove ethanol-soluble organic matters and water. The ethanol-insoluble matter was dried under reduced pressure to obtain a powderous milt extract.

The thus obtained milt extract was a pale grayish white powder and had the following chemical and physical properties:

| | |
|---|---|
| Weight Ratio of Nucleic Acid to Protein: | from 1.0:1.0 to 2.0:1.0 |
| Nucleic acid content: | 25–50 wt % |
| Protein Content: | 25–50 wt % |
| Mineral Content: | 5–15 wt % |
| Total Nitrogen Content: | 13–20 wt % |
| Ninhydrin Reaction: | positive |

In the same manner as described above, milt extracts were obtained from fish of other kinds.

FORMULATION EXAMPLE 1

| | |
|---|---|
| Milt extract as prepared in Preparation Example 1 | 3.0 g |
| Sodium salt of vitamin C | 6.0 g |
| Total: | 9.0 g |

The above ingredients were each pulverized to a particle size of 350 μm or smaller and were weighed and uniformly mixed in a V-type mixer to prepare powders.

FORMULATION EXAMPLE 2

| | |
|---|---|
| Milt extract as prepared in Preparation Example 1 | 3.0 g |
| Sodium salt of vitamin C | 10.0 g |
| Total: | 13.0 g |

The above ingredients were each pulverized to a particle size of 350 μm or smaller and were weighed and uniformly mixed in a V-type mixer to prepare powders.

FORMULATION EXAMPLE 3

| | |
|---|---|
| Milt extract as prepared in Prepartion Example 1 | 8.5 g |
| Sodium salt of vitamin C | 42.5 g |
| Rose hip | 3.0 g |
| Calcium pantothenate | 1.0 g |
| Powdered sugar | 15.0 g |
| Lactose | 40.0 g |
| Total: | 110.0 g |

The above ingredients were weighed and uniformly mixed to prepare granules.

FORMULATION EXAMPLE 4

| | |
|---|---|
| Milt extract as prepared in Preparation Example 1 | 8.5 g |
| Sodium salt of vitamin C | 42.5 g |
| Powdered sugar | 9.86 g |
| Lactose | 25.0 g |
| Rose hip | 3.0 g |
| Additives (flavors, lubricants, etc.) | 11.14 g |
| Total: | 100.0 g |

The above ingredients were weighed and uniformly mixed in a V-type mixer. The resulting powder mixture was directly pounched out to prepare tablets each weighing 1 g.

CLINICAL EXAMPLES

Nucleic acids alone or the powder preparations as prepared in Formulation Examples 1 or 2 were administered to patients who had fasted and only ingested an artificial nutrient which did not contain any nucleic acids. The blood uric acid levels of these patients were measured at prescribed intervals.

Case (1): Administration of Nucleic Acids Alone

Figure 1:
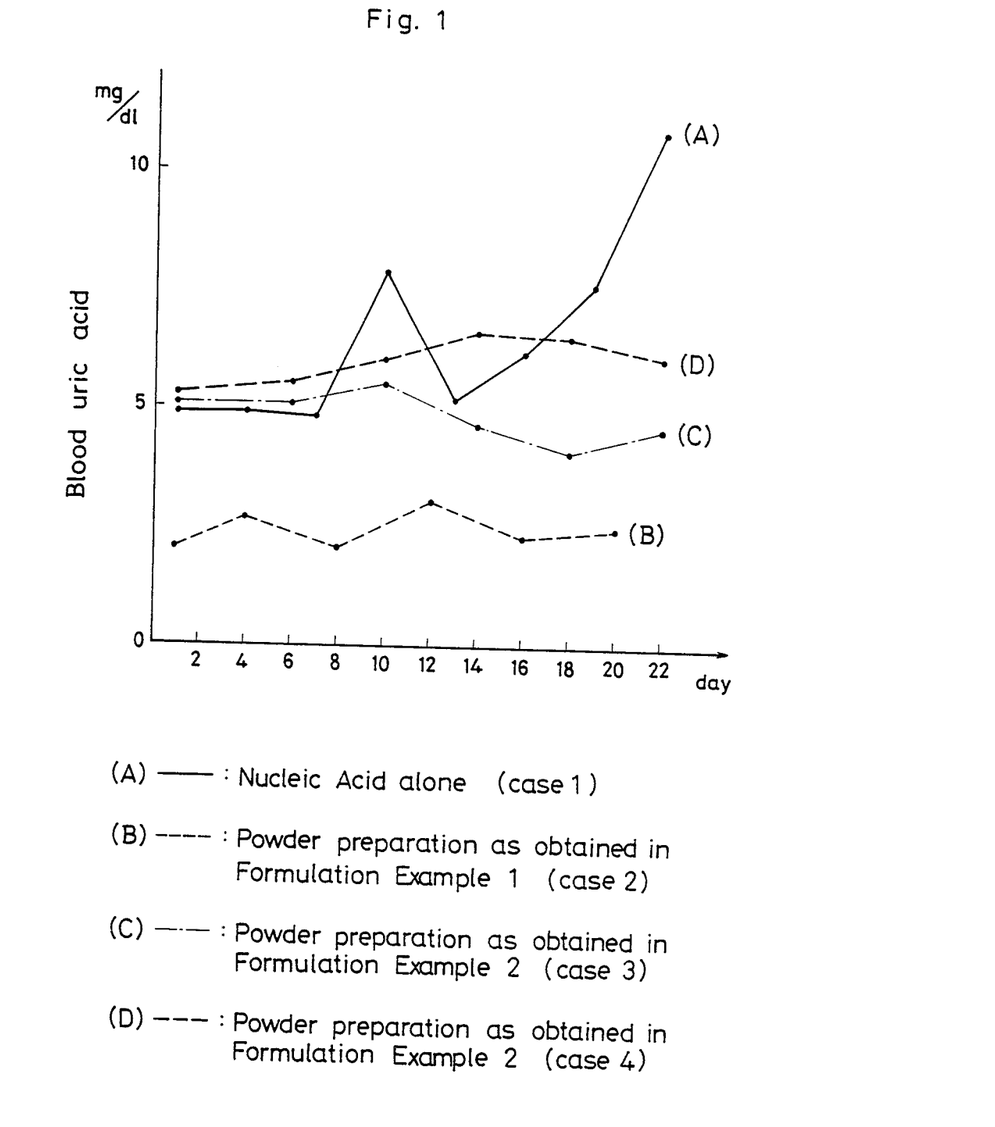
FIG. 1 shows the results of measurement of blood uric acid levels at prescribed intervals in clinical cases (1) to (4) for individuals who had fasted and ingested only an artificial nutrient that did not contain nucleic acids. These individuals received a supplement of nucleic acids alone or a powder preparation (nucleic acids plus a sodium salt of vitamin C) according to the present invention.

Only the milt extract as used in the powder preparation of Formulation Example 1 was administered to a 78-year-old male patient suffering from cerebral infarct and ischemic malum cordis. The dose was 3.0 g/day from the day after starting a blood uric acid level measurement (i.e., the 2nd day in FIG. 1) through the 22nd day, and the uric acid level in blood was determined every several days. The results obtained are shown in FIG. 1.

Case (2): Administration of Powder Preparation (milt extract plus sodium salt of Vitamin C)

The powder preparation as prepared in Formulation Example 1 was administered to a 58-year-old female patient who suffered from ovarian cancer and cancerous peritonitis and who was maintained on Cysnoplatin (an anticancer agent) at a a dose of 9.0 g per day from the day after starting a blood uric acid level measurement (i.e., the 2nd day in FIG. 1) to the 20th day. The uric acid level in blood was measured every several days. The results obtained are shown in FIG. 1.

Case (3): Administration of Powder Preparation (milt extract plus sodium salt of Vitamin C)

A daily dose of 13.0 g of the powder preparation as prepared in Formulation Example 2 was consecutively administered to a 55-year-old male patient suffering from cerebral infarct from the day after starting a blood uric acid level measurement (i.e., the 2nd day in FIG. 1) to the 22nd day, and the blood uric acid level was determined every several days. The results obtained are shown in FIG. 1.

Case (4): Administration of Powder Preparation (milt extract plus sodium salt of Vitamin C)

A daily dose of 13.0 g of the powder preparation as prepared in Formulation Example 2 was administered to a 49-year-old male patient with primary liver cancer which had spread to the backbone and the left lung by metastatis. The administration was carried out from the first day of starting a blood uric acid level measurement to the 22nd day. The blood uric acid level in blood was measured every several days, and the results obtained are shown in FIG. 1.

As can be seen in FIG. 1, the blood uric acid level in the case of administration of nucleic acids alone shows a rising tendency, whereas in each case of administering the powder preparations according to the present invention, the blood uric acid level remains normal without any sign of rising.

Cases (5) to (8)

To each of three of four patients who had been maintained on 500 mg a day of 5-fluorouracil (an anticancer agent), was administered a daily dose of 3 g of the milt extract derived from salmon as used in Formulation Example 1 (Case (5)), a daily dose of 10 g of vitamin C (Case (6)), or a daily dose of 10 g of the powder preparation as obtained in Formulation Example 1 (Case (7)). As a control, no chemical was administered to one of the four patients (Case (8)). The leucocytes and platelets in blood were counted in each case every 30 days for a period of 180 days. The results obtained are shown in FIGS. 2 and 3, respectively.

Figure 2:
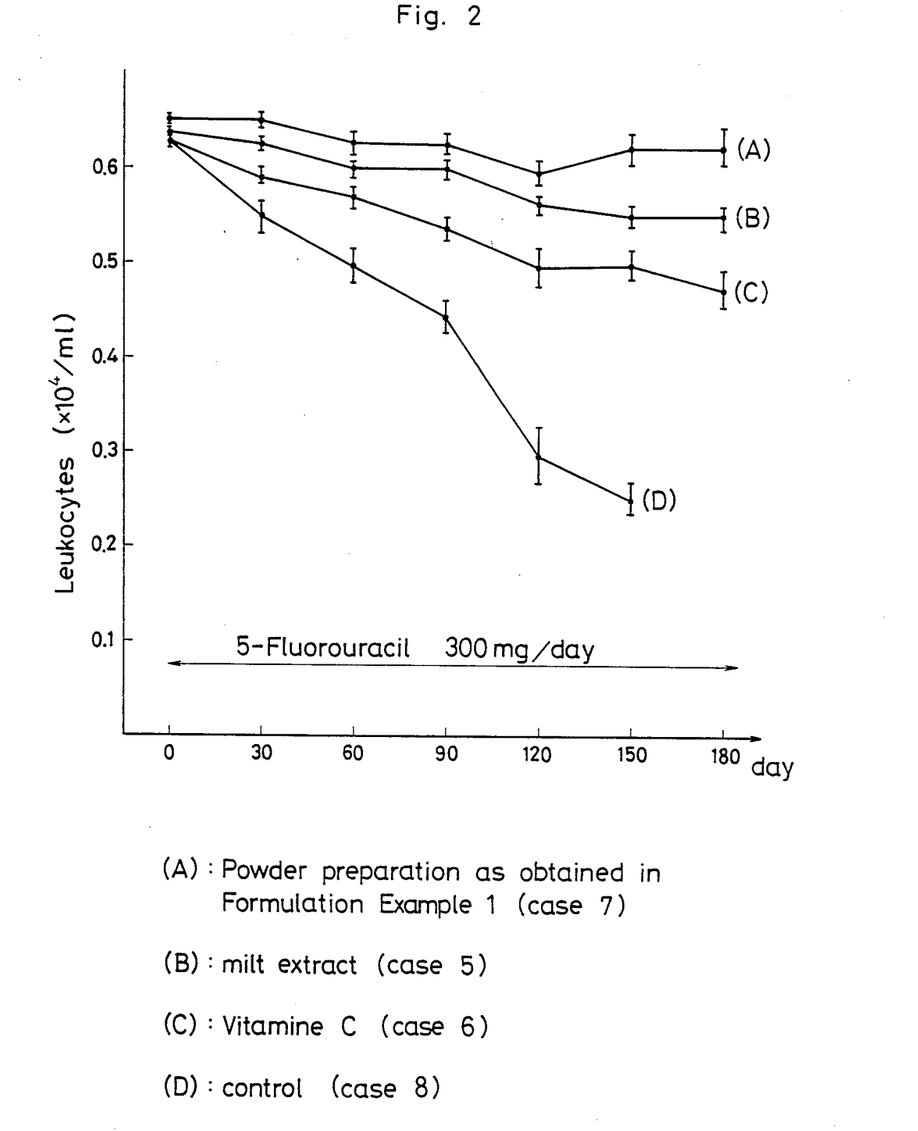
FIGS. 2 and 3 each illustrate changes in the number of leucocytes or blood platelets, respectively, when a composition of the present invention was administered to patients who had been maintained on 5-fluorouracil, an anticancer agent.
Figure 3:
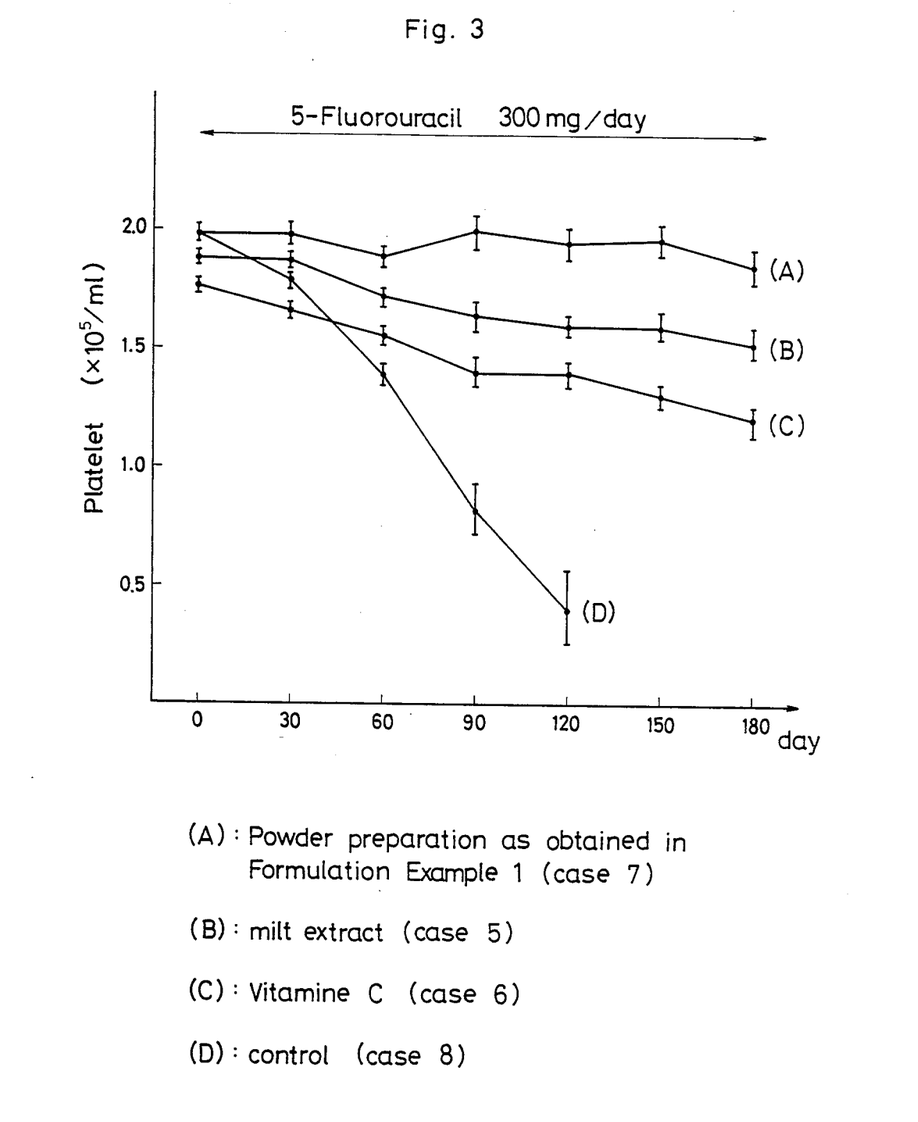

As is apparent from FIGS. 2 and 3, it can be seen that the composition according to the present invention markedly suppresses the reduction of blood platelets and leucocytes which is attributed to administration of 5-fluorouracil and, thus, recovers the hematopoietic function of hematopoietic organs, particularly the bone marrow.

Cases (9) to (11)

To each of three patients who had been placed on a 300 mg a day dose of 5-fluorouracil (an anticancer agent), was administered a daily dose of 3 g of the milt extract as used in the Formulation Example 1 (Case (9)), a daily dose of 10 g of vitamin C (Case (10)), or a daily dose of 10 g of the powder preparation as prepared in Formulation Example 1 (Case (11)). The uric acid level in blood in each patient was measured every 30 days for a period of 180 days. The results obtained are shown in FIG. 4.

Figure 4:
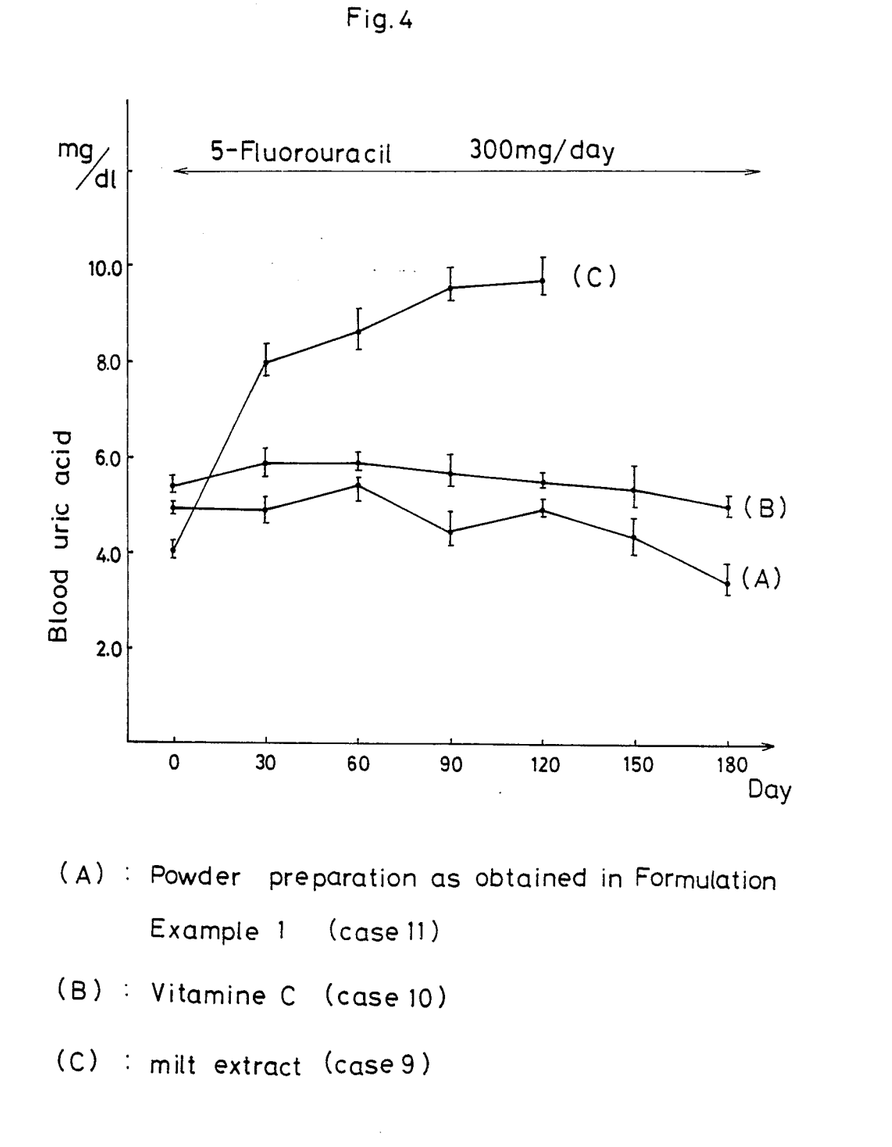
FIG. 4 shows changes of blood uric acid levels in the same patients as in FIGS. 2 and 3.

The results of FIG. 4 demonstrate that the composition of the present invention suppresses an increase of blood uric acid levels and is, therefore, free from any possibility of causing complications, such as gouty arthritis, tophus, renal disorders, urolithiasis, arteriosclerosis, etc., in patients during medical treatment.

Case (21): Administration example of the powder preparation to an anemic patient To a hospitalized 70-year-old male patient who was recognized as having anemic symptoms was continuously administered a daily dose of 10 g of the powder preparation of Formulation Example 1.

Observation is as follows:

The decrease of hematopoietic function of the bone marrow due to anemic disease was determined by examining normal serum iron and by sternal puncture. Moreover, observation was conducted as to leucocytes, erythrocytes, hemoglobins, hematocrit and blood platelets.

Figure 5:
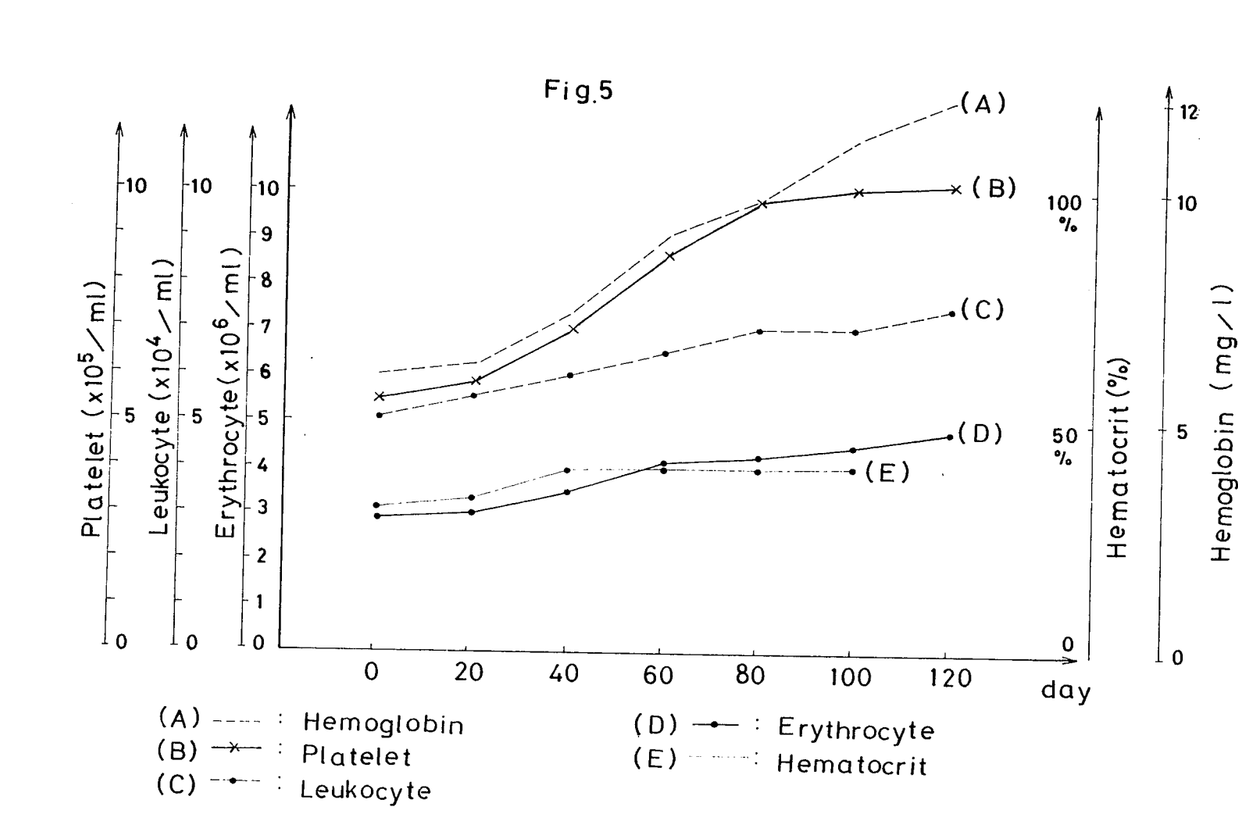
FIG. 5 shows changes of leucocytes, blood platelets, erythrocytes, hemoglobins and hematocrit respectively, when a composition of the present invention was administered to an anemic patient.

The result is shown in FIG. 5.

As apparent from the changes shown in FIG. 5, observation of peripheral blood showed gradual recovery and normal blood was observed after about three months.

Further, it has been revealed that the method according to the present invention which comprises orally administering the composition particularly to patients with cancers is effective for recovery of physical strength and is, therefore, an excellent nutritional auxotherapy.

While the present invention has been described in detail and with reference to specific embodiments thereof, it will be apparent to one skilled in the art that various changes and modifications can be made therein without departing from the spirit and scope thereof.

What is claimed is:

1. A method for improving the hematopoietic function of bone marrow of a patient having a reduced hematopoietic function of bone marrow, which comprises orally administering to said patient a composition comprising milt extract from salmon, porgies, herrings, cods, sardines, swell fishes or bonitoes and at least one of vitamin C or a pharmaceutically acceptable salt thereof, said composition having a weight ratio of said at least one of vitamin C or a pharmaceutically acceptable salt thereof to said milt extract sufficient to inhibit an increased uric acid level in serum which occurs from administration of said milt extract.

2. A method as claimed in claim 1, wherein said patient has said reduced hematopoietic function of bone marrow as a result of being administered an anticancer medicine.

3. A method as claimed in claim 1, wherein said patient has said reduced hematopoietic function of bone marrow as a result of being administered radiotherapy for curing cancer.

4. A method as claimed in claim 1, wherein said patient has said reduced hematopoietic function of bone marrow as a result of being ill.

5. A method as claimed in claim 1, wherein said milt extract is derived from salmon.

6. A method as claimed in claim 1, wherein said milt extract comprises:
    (a) 25–50 weight % deoxyribonucleic acids;
    (b) 25–50 weight % of a protein selected from the group consisting of histone and protamine;
    (c) 5–15 weight % minerals; and
    (d) 13–20 weight % nitrogen;
wherein a weight ratio of said deoxyribonucleic acids to said protein is from 1.0:1.0 to 2.0:1.0 and wherein said milt extract is positive in ninhydrin reaction.

7. A method as claimed in claim 1, wherein said composition is administered at a dose of from 1 to 50 g per day.

8. A method as claimed in claim 7, wherein said composition is administered at a dose of from 10 to 40 g per day.

9. A method as claimed in claim 1, wherein said milt extract is administered at a dose of from 0.1 to 10 g per day.

10. A method as claimed in claim 9, wherein said milt extract is administered at a dose of from 0.2 to 5 g per day.

11. A method for improving the hematopoietic function of bone marrow of a patient having a reduced hematopoietic function of bone marrow, which comprises orally administering to said patient at a dose rate of from 10 to 40 g per day, a composition comprising milt extract from salmon, porgies, herrings, cods, sardines, swell fishes or bonitoes and at least one vitamin C, or a pharmaceutically acceptable salt thereof, said composition having a weight ratio of said at least one of vitamin C or a pharmaceutically acceptable salt thereof to said milt extract sufficient to inhibit an increased uric acid level in serum which occurs from administration of said milt extract, wherein said milt extract comprises:

(a) 25-50 weight % deoxyribonucleic acids;
(b) 25-50 weight % of a protein selected from the group consisting of histone and protamine;
(c) 5-15 weight % minerals; and
(d) 13-20 weight % nitrogen;

wherein a weight ratio of said deoxyribonucleic acids to said protein is from 1.0:1.0 to 2.0:1.0 and wherein said milt extract is positive in ninhydrin reaction.

12. A method as claimed in claim 1, wherein said weight ratio is 1 to 100:1.

13. A method as claimed in claim 1, wherein said weight ratio is 1 to 5:1.

14. A method as claimed in claim 11, wherein said weight ratio is 1 to 100:1.

15. A method as claimed in claim 11, wherein said weight ratio is 1 to 5:1.

* * * * *